United States Patent
Zhong et al.

(10) Patent No.: US 8,318,772 B2
(45) Date of Patent: Nov. 27, 2012

(54) AMINE COMPOUNDS AND MEDICAL USES THEREOF

(75) Inventors: Bohua Zhong, Beijing (CN); Youzhi Zhang, Beijing (CN); Yanping Zhang, Beijing (CN); Rui Xue, Beijing (CN); Xinhua He, Beijing (CN); Yunfeng Li, Beijing (CN); Hongxia Chen, Beijing (CN); Nan Zhao, Beijing (CN); Meiying Li, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 13/001,379

(22) PCT Filed: Jun. 23, 2009

(86) PCT No.: PCT/CN2009/000697
§ 371 (c)(1),
(2), (4) Date: Apr. 1, 2011

(87) PCT Pub. No.: WO2009/155786
PCT Pub. Date: Dec. 30, 2009

(65) Prior Publication Data
US 2011/0178127 A1      Jul. 21, 2011

(30) Foreign Application Priority Data
Jun. 23, 2008   (CN) ................. 2008 1 0127171

(51) Int. Cl.
| | |
|---|---|
| *A61K 31/4535* | (2006.01) |
| *A61K 31/4025* | (2006.01) |
| *A61K 31/381* | (2006.01) |
| *A61K 31/357* | (2006.01) |
| *A61K 31/36* | (2006.01) |
| *C07D 407/12* | (2006.01) |
| *C07D 409/14* | (2006.01) |
| *C07D 409/12* | (2006.01) |

(52) U.S. Cl. ........ 514/321; 514/422; 514/444; 514/452; 514/466; 546/197; 548/526; 549/60; 549/362; 549/435

(58) Field of Classification Search .................. 514/321, 514/444, 422, 466, 452; 549/60, 435, 362; 548/526; 546/197
See application file for complete search history.

(56) References Cited

U.S. PATENT DOCUMENTS
4,018,895 A      4/1977   Molloy et al.

FOREIGN PATENT DOCUMENTS
| CN | 87 1 08175 | 7/1988 |
|---|---|---|
| EP | 0 273 658 | 7/1988 |

OTHER PUBLICATIONS

Martínez-Esparza et al., "New 1-Aryl-3-(4-arylpiperazin-1-yl)propane Derivatives, with Dual Action at 5-HT$_{1A}$ Serotonin Receptors and Serotonin Transporter, as a New Class of Antidepressants," *J. Med. Chem.* 44:418-428, 2001.
Russian Office Action for corresponding Russian Application No. 2011102396 with English translation, dated Mar. 1, 2012, 4 pages.

*Primary Examiner* — Kristin Bianchi
(74) *Attorney, Agent, or Firm* — Seed IP Law Group PLLC

(57) ABSTRACT

The present invention relates to a new amine compound or a pharmaceutically acceptable salt thereof, wherein the definitions of X, $R_1$, $R_2$ and n are given in the description, to a pharmaceutical composition containing the compound as active ingredient, and to use of the amine compound or its pharmaceutically acceptable salt for the manufacture of an anti-depressent drug.

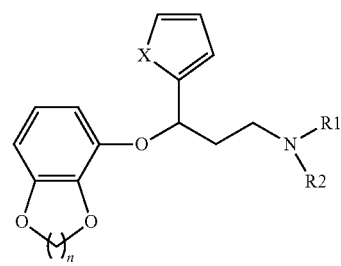

8 Claims, No Drawings

AMINE COMPOUNDS AND MEDICAL USES THEREOF

CROSS-REFERENCE TO RELATED APPLICATIONS

This application is a U.S. national stage application filed under 35 U.S.C. §371 of International Patent Application No. PCT/CN2009/000697, accorded an international filing date of Jun. 23, 2009, which claims the benefit of priority to Chinese (CN) Patent Application No. 200810127171.5, filed Jun. 23, 2008, all of which applications are incorporated herein by reference in their entirety.

TECHNICAL FIELD

The present invention relates to new amine compounds or pharmaceutically acceptable salts thereof, pharmaceutical compositions containing such compounds as an active ingredient, and uses of such amine compounds or pharmaceutically acceptable salts thereof for manufacture of antidepressant drugs.

BACKGROUND

Depression is the most common nerval and mental disorder that seriously affects physical and psychological health of people. With the acceleration of living tempo and the elevation of social pressure, the incidence of depression increases significantly.

Treatments with drugs are main means for treatment of depression. Principal therapeutical drugs include: tricyclic antidepressant drugs such as imipramine, amitriptyline, etc.; monoamine oxidase inhibitors such as moclobemide, etc.; selective serotonin reuptake inhibitors such as fluoxetine, sertraline, etc.; selective noradrenaline reuptake inhibitors such as reboxetine, etc.; dual noradrenergic/serotonergic inhibitors such as mirtazapine, etc.; dual serotonin/noradrenaline reuptake inhibitors such as venlafaxine, Duloxetine, etc. Currently, these commonly used drugs usually have drawbacks of slow onset, low efficiency and significant toxic and side effects and the like.

U.S. Pat. No. 4,018,895 discloses antidepressant drugs including fluoxetine, which have the following formula:

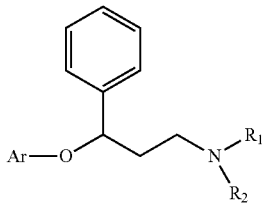

wherein Ar is naphthalene ring or substituted benzene ring, and $R_1$ and $R_2$ independently are H or $CH_3$.

Chinese Patent CN1019113 discloses antidepressant drugs including Duloxetine, which have the following formula:

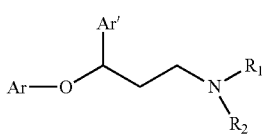

wherein Ar is naphthalene ring or substituted benezene ring, Ar' is cycloalkyl, thienyl, furyl or thiazolyl, $R_1$ and $R_2$ independently are H or $CH_3$.

CONTENTS OF THE INVENTION

The present invention provides an amine compound represented by Formula I or a pharmaceutically acceptable salt thereof:

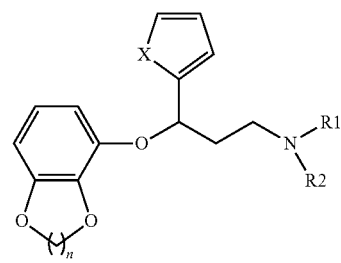

I wherein,

X represents S or O;

$R_1$ and $R_2$ independently represent H or $C_{1-4}$alkyl, or $R_1$ and $R_2$ together with N atom to which they are attached can form a 5- or 6-membered heterocyclic ring; and n is 1 or 2.

In the second aspect, the present invention relates to a method for preparing a compound of Formula I or a pharmaceutically acceptable salt thereof.

In the third aspect, the present invention relates to a pharmaceutical composition comprising a compound of Formula I or a pharmaceutically acceptable salt thereof as well as one or more pharmaceutically acceptable carriers or excipients.

In the fourth aspect, the present invention relates to use of a compound of Formula I or a pharmaceutically acceptable salt thereof for manufacturing an antidepressant drug.

Therefore, according to one embodiment of the present invention, the present invention provides an amine compound represented by the Formula I or a pharmaceutically acceptable salt thereof:

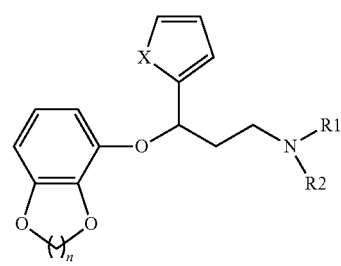

I wherein,

X represents S or O;

$R_1$ and $R_2$ independently represent H or a $C_{1-4}$alkyl, or $R_1$ and $R_2$ together with N atom to which they are attached can form a 5- or 6-membered heterocyclic ring; and n is 1 or 2.

According to the present invention, the term "5- or 6-membered heterocyclic ring" includes but is not limited to pyrrole ring, piperidine ring, etc.

According to another embodiment of the present invention, the present invention provides an amine compound of the Formula I or a pharmaceutically acceptable salt thereof:

wherein,

X represents S or O;

$R_1$ and $R_2$ independently represent H or a $C_{1-4}$alkyl; and n is 1 or 2.

According to one preferred embodiment of the present invention, the present invention provides an amine compound of the Formula I or a pharmaceutically acceptable salt thereof:

I wherein,

X represents S or O;

$R_1$ and $R_2$ independently represent H, methyl or ethyl; and n is 1 or 2.

The present more preferably provides the following compounds:

N,N-dimethyl-3-[(benzo[1,3]dioxolan-4-yl)-oxy]-3-(thiophen-2-yl)-propylamine.oxalate;

N-methyl-3-[(benzo[1,3]dioxolan-4-yl)-oxy]-3-(thiophen-2-yl)-propylamine.oxalate;

N,N-diethyl-3-[(benzo[1,3]dioxolan-4-yl)-oxy]-3-(thiophen-2-yl)-propylamine.oxalate;

1-[3-(benzo[1,3]dioxolan-4-yl-oxy)-3-(thiophen-2-yl)-propyl]-pyrrolidine.oxalate;

1-[3-(benzo[1,3]dioxolan-4-yl-oxy)-3-(thiophen-2-yl)-propyl]-piperidine.oxalate;

N,N-dimethyl-[3-(benzo[1,3]dioxolan-4-yl-oxy)-3-(furan-2-yl)]-propylamine.oxalate;

N-methyl-[3-(benzo[1,3]dioxolan-4-yl-oxy)-3-(furan-2-yl)]-propylamine.oxalate;

N,N-dimethyl-3-[(benzo[1,4]dioxan-5-yl-oxy)-3-(thiophen-2-yl)-propylamine].oxalate;

N-methyl-3-[(benzo[1,4]dioxan-5-yl-oxy)-3-(thiophen-2-yl)-propylamine].oxalate; and N,N-dimethyl-3-[(benzo[1,4]dioxan-5-yl-oxy)-3-(furan-2-yl)propylamine].oxalate.

The amine compounds of the present invention can be prepared according to a method shown in following scheme:

Specifically, acetyl thiophene or acetyl furan and a dialkyl amine as well as paraformaldehyde are dissolved in anhydrous ethanol. The mixture is adjusted to a pH value of 3-4 with concentrated hydrochloric acid, heated to reflux for 6-10 h to obtain 3-dialkylamino-1-(thiophen/furan-2-yl)-1-acetone hydrochloride. The free base is obtained by alkalisation, and reacts with $LiAlH_4$ to obtain a hydroxyl derivative in which the reaction solvent is anhydrous tetrahydrofuran, the reaction temperature is −5° C. to room temperature and the reaction time is 1-5 h; the hydroxyl derivative reacts with 4-hydroxyl-benzo[1,3]dioxolane or 5-hydroxyl-benzo[1,4] dioxane in the presence of triphenylphosphine and diethyl azodicarboxylate to obtain a target compound with a dialkyl substituted on the nitrogen atom, in which the reaction solvent is anhydrous tetrahydrofuran, the reaction temperature is −5° C. to room temperature and the reaction time is 12-36 h; the target compound with a dialkyl substituted on the nitrogen atom is subjected to the action of phenyl chloroformate to remove one substituent thereon to obtain a target compound with a monoalkyl substituted on the nitrogen atom.

Similarly, tetrahydropyrrole or piperidine can be used to replace dialkylamine to carry out the above reaction to obtain a target compound in which $R_1$ and $R_2$ together with the N atom to which they are attached form a 5- or 6-membered heterocyclic ring.

The free base of the target compound reacts with a corresponding acid to obtain a salt of the target compound.

The present invention further provides pharmaceutically acceptable salts of the amine compounds of the Formula I, in which these salts can be formed by reacting the amino group of the amine compounds of the Formula I with various inorganic acids such as hydrochloric acid, sulfuric acid, hydrobromic acid or phosphoric acid, or formed by reacting the amino group of an amine compounds of the Formula I with various organic acids such as oxalic acid, maleic acid, benzoic acid, fumaric acid, etc. Oxalate is preferred.

The present invention further provides a pharmaceutical composition comprising an amine compound of the Formula I or a pharmaceutically acceptable salt thereof as an active ingredient as well as a suitable carrier or excipient. The carrier or excipient includes but is not limited to ion exchanger, alumina, aluminum stearate, lecithin, serum proteins such as human serum albumin, buffer substances such as phosphate, glycerol, sorbic acid, potassium sorbate, a mixture of partial glycerides of saturated plant fatty acids, water, salt or electrolyte, such as protamine sulfate, disodium hydrogen phosphate, potassium hydrogen phosphate, sodium chloride, zinc salt, colloidal silicon dioxide, magnesium trisilicate, polyvinylpyrrolidone, cellulosic substances, polyethylene glycol, sodium carboxymethylcellulose, polyacrylates, bee wax, lanoline, etc. The pharmaceutical composition of the present invention can be formulated to the form of solution, tablet, capsule or injection by conventional methods known by the person skilled in the art.

The amine compounds of Formula I or pharmaceutically acceptable salts thereof as well as a pharmaceutical composition thereof according to the present invention can be used for the antidepressive treatment.

The amine compounds of Formula I or pharmaceutically acceptable salts thereof or a pharmaceutical composition thereof according to the present invention can be administered by oral, parenteral such as subcutaneous, intravenous, intramuscular or intraperitoneal route, or via an externally explanted reservoir. Oral or injection administration is preferred.

In addition, it is noted that the dosage and method of use of the present compounds depend on many factors including age, body weight, gender, physical health condition, nutritional state, strength of compound, duration of administration, metabolic rate, severity of the conditions to be treated and the subjective judgment of the medicine. The preferred dosage of administration is 0.01-100 mg/kg body weight/day, and the most preferred dosage of administration is 0.1-10 mg/kg body weight/day.

CONCRETE MODES FOR CARRYING OUT THE INVENTION

The following examples further illustrate the present invention but are not intended to limit the scope of the present invention. The skilled in the art would understand that the present invention can be varied and modified without departing from the scope of spirit of the present invention.

Example 1

Preparation of N,N-dimethyl-3-[(benzo[1,3]dioxolan-4-yl)-oxy]-3-(thiophen-2-yl)-propylamine.oxalate ($I_1$)

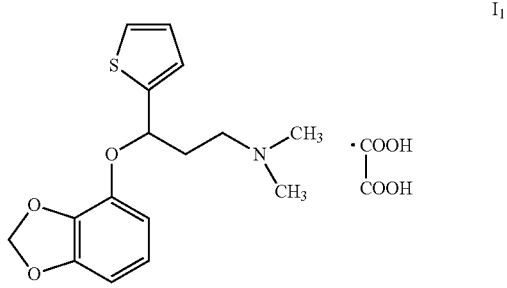

1.1: Preparation of 3-dimethylamino-1-(thiophen-2-yl)-1-acetone.hydrochloride 2-Acetylthiophene (20.0 g, 0.16 mol), dimethylamine hydrochloride (16.8 g, 0.21 mol), paraformaldehyde (9.5 g, 0.32 mol) and 50 mL anhydrous ethanol were placed into a 150 mL three-necked bottle, The mixture was added with concentrated hydrochloric acid to reach a pH of 3-4, and heated to reflux for 8 h. The reaction was stopped, and the reaction mixture was cooled to room temperature, frozen overnight, and filtrated in vacuum. The filter cake was washed with cold anhydrous ethanol to be white to obtain 31.2 g of white crystal with a yield of 89.6%. MS (m/e): 184.3 (M+1$^+$).

1.2: Preparation of 3-dimethylamino-1-(thiophen-2-yl)-1-propanol

3-Dimethylamino-1-(2-thienyl)-1-acetone hydrochloride (30.8 g, 0.14 mol) was dissolved in 150 ml distilled water. The mixture was added dropwise with 2.5 M sodium hydroxide aqueous solution to reach a pH of about 10, extracted with ethyl acetate (100 ml×3). The organic phases were combined and washed with saturated sodium chloride anqueous solution twice, dried over anhydrous sodium sulfate, and distilled under a reduced pressure to remove ethyl acetate, thereby obtaining a yellow oily liquid. The liquid was dissolved in 30 ml anhydrous tetrahydrofuran, the mixture was slowly added dropwise to the solution of LiAlH$_4$ (7.8 g, 0.21 mol) in 100 ml anhydrous tetrahydrofuran, and the reaction temperature was controlled at 0-5° C. in an ice bath. The ice bath was removed, and the reaction was performed at room temperature for 2 h and stopped. The reaction liquid was added dropwise with anhydrous ethanol slowly, and the solids were removed by filtration under vacuum after the residual LiAlH$_4$ was completed. Tetrahydrofuran was distilled out under a reduced pressure and the residue was extracted with dichloromethane (50 ml×3). The organic phases were combined, washed with saturated sodium chloride aqueous solution twice, dried over anhydrous sodium sulfate, and distilled to remove dichloromethane, to obtain 22.9 g of 3-dimethylamino-1-(thiophen-2-yl)-1-propanol as a white solid in a yield of 88.3%. $^1$H-NMR δ (ppm, CD$_3$COCD$_3$-d$_6$): 7.28-7.30 (dd, 1H, Ar—H); 6.92-6.96 (m, 2H, Ar—H); 5.06-5.09 (t, 1H, CHOH); 2.87 (s, 1H, OH); 2.55-2.62 (m, 1H, CH$_2$N); 2.40-2.47 (m, 1H, CH$_2$N); 2.23 (s, 6H, N(CH$_3$)$_2$); 1.86-1.91 (m, 2H, CH$_2$CH$_2$N).

1.3: Preparation of N,N-dimethyl-3-[(benzo[1,3]dioxolan-4-yl)-oxy]-3-(thiophen-2-yl)-propylamine.oxalate (Compound I$_1$)

3-Dimethylamino-1-(thiophen-2-yl)-1-propanol (1.85 g, 0.01 mol), 4-hydroxyl-benzo[1,3]dioxolane (1.38 g, 0.01 mol) and triphenylphosphine (3.93 g, 0.015 mol) were dissolved in 80 ml of anhydrous tetrahydrofuran. The mixture was slowly added dropwise with the solution of diethyl azodicarboxylate (2.61 g, 0.015 mol) in 20 ml anhydrous tetrahydrofuran, the reaction temperature was controlled to be lower than −5° C. in an ice-salt bath. After completion of the addition, the ice-salt bath was removed, and the reaction was performed at room temperature for 24 h. After the end of reaction, tetrahydrofuran was distilled out under a reduced pressure, the resultant oily liquid was dissolved in 100 ml of ethyl acetate, washed with diluted sodium hydroxide aqueous solution and saturated sodium chloride aqueous solution separately once, dried over anhydrous sodium sulfate, and separated by silica gel column chromatography to obtain 1.07 g of N,N-dimethyl-3-[(benzo[1,3]dioxolan-4-yl)-oxy]-3-(thiophen-2-yl)-propylamine as a pale yellow oily liquid, which was dissolved in 30 ml of ethyl acetate, added with oxalic acid (0.32 g, 0.035 mol) to generate a pale yellow solid. The mixture was heated to reflux, cooled to room temperature, frozen for 2 h and filtrated. The filter cake was washed with cold ethyl acetate to obtain 1.31 g of the target compound as a pale yellow powdery solid in a yield of 33.2% and a melting point of 85-88° C. MS (m/e): 306.5 (M+1$^+$); $^1$H-NMR δ (ppm, DMSO-d$_6$): 7.46-7.48 (d, 1H, 5'-H); 7.11-7.12 (d, 1H, 3'-H); 6.95-6.97 (dd, 1H, 4'-H); 6.66-6.70 (t, 1H, 6-H); 6.53-6.59 (dd, 2H, 5,7-H); 5.97-5.98 (d, 2H, 2-H); 5.71-5.75 (t, 1H, CHO); 2.27-2.30 (t, 2H, CH$_2$N); 2.19-2.21 (m, 1H, CH$_2$CH$_2$N); 2.11 (s, 6H, N(CH$_3$)$_2$); 2.06-2.08 (m, 1H, CH$_2$CH$_2$N).

Example 2

Preparation of N-methyl-3-[(benzo[1,3]dioxolan-4-yl)-oxy]-3-thiophen-2-yl)-propylamine.oxalate (compound I$_2$)

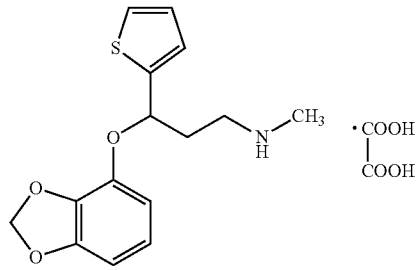

N,N-dimethyl-3-[(benzo[1,3]dioxolan-4-yl)-oxy]-3-(thiophen-2-yl)-propylamine (1.26 g, 4.14 mmol) was dissolved in 50 ml of anhydrous toluene. The mixture was heated to reflux, added dropwise over 0.5 h with the solution of phenyl chloroformate (0.78 g, 4.97 mmol) in 10 ml anhydrous toluene. After completion of the addition, the refluxing was maintained for 1 h, and then the reaction was terminated, and cooled to room temperature. The organic phase was washed with 2.5M sodium hydroxide aqueous solution (20 mL×3), the organic phase was washed with distilled water to neutral, then with 1.0M hydrochloric acid aqueous solution (20 mL×3), with distilled water to neutral, with saturated sodium chloride aqueous solution, dried over anhydrous sodium sulfate, filtered to remove the drying agent, and distilled under a reduced pressure to remove toluene to obtain a pale yellow oil.

40 mL of 1,2-propylene glycol was added to the above oil, sodium hydroxide (1.65 g, 4.14 mmol) was dissolved in 10 mL of distilled water and added to the above 1,2-propylene glycol solution. The mixture was heated to reflux for 3 h, the reaction was then terminated, cooled to room temperature, added with diluted hydrochloric acid aqueous solution to adjust the pH of about 3, stirred at room temperature for 1 h, extracted with n-hexane (30 mL×3), added with sodium hydroxide aqueous solution to adjust a pH of about 10, extracted with ethyl acetate (30 mL×3). The organic phase was washed with saturated saline solution, dried over anhydrous sodium sulfate, filtered to remove the drying agent, and distilled under a reduced pressure to remove solvent to a residue of about 20 mL. The residue was then added with 0.37 g (4.14 mmol) of oxalic acid to generate a white precipitate. The mixture was heated to reflux for 0.5 h, cooled to room temperature, frozen for 4 h. After filtration under vacuum, the filter cake was washed with cold ethyl acetate to obtain 0.34 g of the target compound as a white powdery solid in a yield of 21.6% and a melting point of 120-123° C. MS (m/e): 292.2 (M+H$^+$), 314.3 (M+Na$^+$). $^1$H-NMR δ (ppm, DMSO-d$_6$): 7.46-7.48 (d, 1H, 5'-H); 7.11-7.12 (d, 1H, 3'-H); 6.95-6.97 (dd, 1H, 4'-H); 6.66-6.70 (t, 1H, 6-H); 6.58-6.60 (d, 2H, 7-H); 6.53-6.55 (d, 1H, 5-H); 5.96-5.98 (dd, 1H, 2-H); 5.76-5.79 (t, 1H, CHO); 2.50-2.52 (t, 2H, CH$_2$N); 2.24 (s, 6H, N(CH$_3$)$_2$); 2.11-2.19 (m, 1H, CH$_2$CH$_2$N); 1.90-1.98 (m, 1H, CH$_2$CH$_2$N).

Example 3

Preparation of N,N-diethyl-3-[(benzo[1,3]dioxolan-4-O-oxy]-3-thiophen-2-yl)-propylamine.oxalate (compound I$_3$)

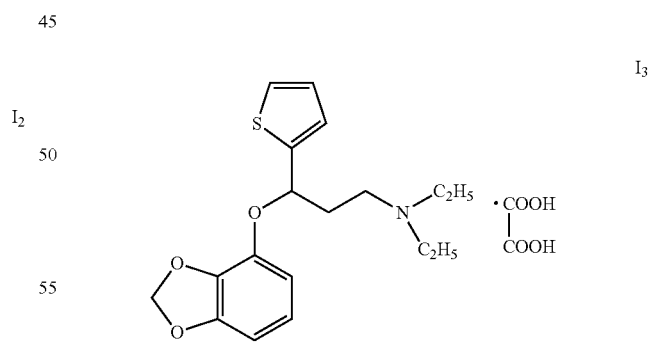

3.1: Preparation of 3-diethylamino-1-(thiophen-2-yl)-1-acetone.hydrochloride 2-Acetylthiophene (20.0 g, 0.16 mol), diethylamine hydrochloride (15.3 g, 0.21 mol), paraformaldehyde (9.5 g, 0.32 mol) and 50 mL anhydrous ethanol were placed in a 150 mL three-necked bottle. The mixture was added dropwise with concentrated hydrochloric acid to reach a pH of 3-4 and heated to reflux for 8 h. The reaction was stopped, cooled to room temperature, frozen overnight, and filtrated under vacuum. The filter cake was washed with cold anhydrous ethanol to white to obtain 31.1 g of 3-diethylamino-1-(thiophen-2-yl)-1-acetone.hydrochloride as a pale yellow crystal in a yield of 78.6%. MS (m/e): 212.3 (M+1$^+$).

3.2: Preparation of 3-diethylamino-1-(thiophen-2-yl)-1-propanol

3-Diethylamino-1-(thiophen-2-yl)-1-acetone.hydrochloride (7.92 g, 0.032 mol) was dissolved in 50 mL of distilled water. The mixture was added dropwise with 2.5M NaOH aqueous solution to reach a pH of about 10, and extracted with ethyl acetate (20 ml×3). The organic phases were combined, washed with saturated sodium chloride aqueous solution twice, dried over anhydrous sodium sulfate, and distilled to remove ethyl acetate. The resultant yellow oily liquid was dissolved in 20 ml of anhydrous tetrahydrofuran, and then added dropwise slowly into the solution of LiAlH$_4$ (1.78 g, 0.048 mol) in 50 ml anhydrous tetrahydrofuran, in which an ice bath was used to control the reaction temperature. After the addition, the ice bath was removed, and the reaction was performed for 2 h and then stopped. Anhydrous ethanol was slowly added dropwise into the reaction liquid. After complete reaction of the residual LiAlH$_4$, solids were removed by filtration under vacuum, tetrahydrofuran was distilled out under a reduced pressure, and the residue was extracted with dichloromethane (20 ml×3). The organic phases were combined, washed with saturated sodium chloride aqueous solution twice, dried over anhydrous sodium sulfate, and distilled to remove dichloromethane to obtain 5.93 g of 3-diethylamino-1-(thiophen-2-yl)-1-propanol as a deep yellow oily liquid in a yield of 87.0%. $^1$H-NMR δ (ppm, DMSO-d$_6$): 7.347.35 (dd, 1H, Ar—H); 6.93-6.95 (dd, H, Ar—H); 6.91-6.92 (dd, H, Ar—H); 5.95 (s, 1H, OH); 4.86-4.89 (t, 1H, CHOH); 2.56-2.37 (m, 6H, CH$_2$N(CH$_2$CH$_3$)$_2$); 1.76-1.81 (m, 2H, CH$_2$CH$_2$N); 0.92-0.95 (m, 6H, N(CH$_2$CH$_3$)$_2$);

3.3: Preparation of N,N-diethyl-3-[(benzo[1,3]dioxolan-4-yl)-oxy]-3-(thiophen-2-yl)-propylamine.oxalate (compound I$_3$)

3-Diethylamino-1-(thiophen-2-yl)-1-propanol (2.11 g, 0.01 mol), 5-hydroxyl-benzo[1,3]dioxolane (1.38 g, 0.01 mol) and triphenylphosphine (3.93 g, 0.015 mol) were dissolved in 80 ml of anhydrous tetrahydrofuran. The mixture was slowly added dropwise with the solution of diethyl azodicarboxylate (2.61 g, 0.015 mol) in 20 ml anhydrous tetrahydrofuran, and an ice-salt bath was used to control the reaction temperature below −5° C. After completion of the addition, the ice-salt bath was removed, and the reaction was performed at room temperature for 24 h. After the end of the reaction, tetrahydrofuran was distilled out under a reduced pressure, and the obtained oily liquid was dissolved in 100 ml of ethyl acetate. The mixture washed with diluted sodium hydroxide aqueous solution and saturated sodium chloride aqueous solution respectively, dried over anhydrous sodium sulfate, and separated by silica gel column chromatography to obtain 1.06 g of the target compound as a pale yellow oily liquid in a yield of 31.8%. MS (m/e): 334.2 (M+1$^+$). $^1$H-NMR δ (ppm, DMSO-d$_6$): 7.25-7.26 (dd, 1H, 5'-H); 6.97-6.98 (d, 1H, 3'-H); 6.81-6.83 (dd, 1H, 4'-H); 6.52-6.56 (t, 1H, 6-H); 6.42-6.44 (d, 1H, 7-H); 6.34-6.36 (d, 1H, 5-H); 5.81-5.82 (d, 2H, 2-H); 5.68-5.71 (t, 1H, CHO); 2.34-2.54 (m, 6H, CH$_2$N(CH$_2$CH$_3$)$_2$); 2.06-2.12 (m, 1H, CH$_2$CH$_2$N); 1.86-1.92 (m, 1H, CH$_2$CH$_2$N); 0.80-0.84 (t, 6H, N(CH$_2$CH$_3$)$_2$).

Example 4

Preparation of 1-[3-(benzo[1,3]dioxolan-4-yl-oxy)-3-(thiophen-2-yl)-propyl]-pyrrolidine.oxalate (compound I$_4$)

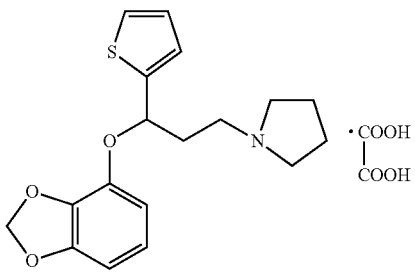

I$_4$ 4.1: Preparation of 3-(tetrahydropyrrol-1-yl)-1-(thiophen-2-yl)-1-acetone.hydrochloride 2-Acetylthiophene (8.82 g, 0.070 mol), tetrahydropyrrole (6.15 g, 0.087 mol), paraformaldehyde (3.90 g, 0.13 mol) and 30 mL of anhydrous ethanol were placed in a 100 mL three-necked bottle. The mixture was added dropwise with concentrated hydrochloric acid to reach a pH of 3-4, and heated to reflux for 8 h. The reaction was stopped, cooled to room temperature, frozen overnight, and filtered. The filter cake was washed with cold anhydrous ethanol to white to obtain 13.3 g of 3-(tetrahydropyrrol-1-yl)-1-(thiophen-2-yl)-1-acetone hydrochloride as a pale yellow crystal in a yield of 77.6%. MS (m/e): 210.4 (M+1$^+$).

4.2: Preparation of 3-(tetrahydropyrrol-1-yl)-1-(thiophen-2-yl)-1-propanol 3-(tetrahydropyrrol-1-yl)-1-(thiophen-2-yl)-1-acetone hydrochloride (12.3 g, 0.050 mol) was dissolved in 50 mL of distilled water. The mixture was added dropwise with 2.5M sodium hydroxide aqueous solution to reach a pH of about 10, and extracted with ethyl acetate (20 mL×3). The organic phases were combined, washed with saturated sodium chloride aqueous solution twice, dried over anhydrous sodium sulfate, and distilled to remove ethyl acetate. The obtained yellow oily liquid was dissolved in 15 ml anhydrous tetrahydrofuran, added dropwise slowly into the solution of LiAlH$_4$ (2.78 g, 0.075 mol) in 50 mL anhydrous tetrahydrofuran, and an ice bath was used to control the reaction temperature. After dropping, the ice bath was removed, and the reaction was performed at room temperature for 2 h and then stopped. Into the reaction liquid, anhydrous ethanol was slowly added dropwise. After complete reaction of the residual LiAlH$_4$, solids were removed by filtration under vacuum, tetrahydrofuran was distilled out under a reduced pressure, and the residue was extracted with dichloromethane (20 mL×3). The organic phases were combined, washed with saturated sodium chloride aqueous solution twice, dried over anhydrous sodium sulfate, and distilled to remove dichloromethane to obtain 8.92 g of a deep yellow oily liquid in a yield of 84.6%. $^1$H-NMR δ (ppm, DMSO-d$_6$): 7.35-7.36 (dd, 1H, Ar—H); 6.93-6.95 (m, H, Ar—H); 6.91-6.92 (m, H, Ar—H); 5.81 (s, 1H, OH); 4.86-4.89 (t, 1H, CHO); 2.40-2.53 (m, 6H, CH$_2$N(CH$_2$CH$_3$)$_2$); 1.78-1.85 (m, 2H, HOCH CH$_2$CH$_2$N); 1.62-1.70 (m, 4H, CH$_2$CH$_2$CH$_2$CH$_2$).

4.3: Preparation of 1-[3-(benzo[1,3]dioxolan-4-yl-oxy)-3-(thiophen-2-yl)-propyl]-pyrrolidine.oxalate (compound I$_4$)

3-(tetrahydropyrrol-1-yl)-1-(thiophen-2-yl)-1-propanol (2.11 g, 0.01 mol), 5-hydroxylbenzo[1,4]dioxolane (1.38 g, 0.01 mol) and triphenylphosphine (3.93 g, 0.015 mol) were dissolved in 80 mL anhydrous tetrahydrofuran. The mixture was slowly added dropwise with the solution of diethyl azodicarboxylate (2.61 g, 0.015 mol) in 20 mL anhydrous tetrahydrofuran, in which the reaction temperature was controlled with an ice-salt bath to be below −5° C. After addition, the ice-salt bath was removed, and the reaction was performed at room temperature for 24 h. After the end of the reaction, tetrahydrofuran was distilled out under a reduced pressure, and the obtained oily liquid was dissolved in 100 mL ethyl acetate. The mixture was washed with diluted sodium hydroxide aqueous solution and saturated sodium chloride aqueous solution respectively, dried over anhydrous sodium sulfate, and separated by silica gel column chromatography to obtain 1.12 g of a pale yellow oily liquid. The oily liquid was dissolved in 30 mL ethyl acetate, added with 0.30 g (0.034 mol) oxalic acid to generate a white solid. The mixture was heated to reflux, cooled to room temperature, frozen for 2 h, and filtrated under vacuum. The filter cake was washed with cooled ethyl acetate to obtain 1.18 g of target compound as a white powdery solid in a yield of 28.2% and a melting point of 105-108° C. MS (m/e): 332.5 (M+H$^+$). $^1$H-NMR δ (ppm, DMSO-d$_6$): 7.47-7.48 (dd, 1H, 5'-H); 7.11-7.12 (d, 1H, 3'-H); 6.95-6.97 (dd, 1H, 4'-H); 6.66-6.70 (t, 1H, 6-H); 6.57-6.59 (d, 1H, 7-H); 6.53-6.55 (d, 1H, 5-H); 5.97-5.98 (d, 2H, 2-H); 5.72-5.75 (t, 1H, CHO); 2.40-2.50 (m, 6H, CH$_2$N (CH$_2$CH$_3$)$_2$); 2.16-2.25 (m, 1H, HOCHCH$_2$CH$_2$N); 1.94-2.03 (m, 1H, HOCHCH$_2$CH$_2$N, 1.67 (s, 4H, CH$_2$CH$_2$ CH$_2$CH$_2$).

Example 5

Preparation of 1-[3-(benzo[1,3]dioxolan-4-yl-oxy)-3-(thiophen-2-yl)-propyl]-piperidine.oxalate (compound I$_5$)

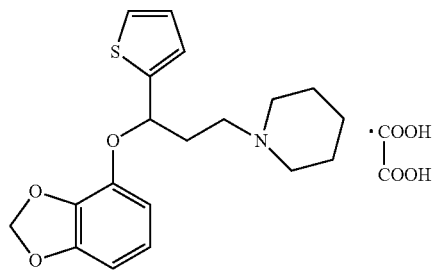

I$_5$ 5.1: Preparation 3-(piperidin-1-yl)-1-(thiophen-2-yl)-1-acetone.hydrochloride 2-Acetylthiophene (8.82 g, 0.070 mol), piperidine (7.37 g, 0.087 mol), paraformaldehyde (3.90 g, 0.13 mol) and 30 mL anhydrous ethanol were placed in a 100 mL three-necked bottle. The mixture was added dropwise with concentrated hydrochloric acid to reach a pH of 3-4 and heated to reflux for 8 h. The reaction was terminated, cooled to room temperature, frozen overnight, and filtrated under vacuum. The filter cake was washed with cold anhydrous ethanol to white to obtain 13.3 g of a pale yellow crystal in a yield of 74.6%. MS (m/e): 224.3 (M+1$^+$).

5.2: Preparation of 3-(piperidin-1-yl)-1-(thiophen-2-yl)-1-propanol 3-(Piperidin-1-yl)-1-(thiophen-2-yl)-1-acetone hydrochloride (13.0 g, 0.050 mol) was dissolved in 50 mL distilled water. The mixture was added dropwise with 2.5M sodium hydroxide aqueous solution to reach a pH of 10, and extracted with ethyl acetate (20 mL×3). The organic phases were combined, washed with saturated sodium chloride aqueous solution twice, dried over anhydrous sodium sulfate, and distilled to remove ethyl acetate. The obtained yellow oily liquid was dissolved in 15 ml anhydrous tetrahydrofuran, added dropwise slowly into the solution of LiAlH$_4$ (2.78 g, 0.075 mol) in 50 mL anhydrous tetrahydrofuran, and the reaction temperature was controlled with an ice bath. After the addition, the ice bath was removed. The reaction was performed at room temperature for 2 h and then stopped. Into the reaction liquid, anhydrous ethanol was slowly added dropwise. After complete reaction of the residual LiAlH$_4$, solids were removed by filtration under vacuum, tetrahydrofuran was distilled out under a reduced pressure, and the residue was extracted with dichloromethane (20 mL×3). The organic phases were combined, washed with saturated sodium chloride aqueous solution twice, dried over anhydrous sodium sulfate, and distilled to remove dichloromethane to obtain 9.26 g of a deep yellow oily liquid in a yield of 82.3%. $^1$H-NMR δ (ppm, DMSO-d$_6$): 7.33-7.34 (dd, 1H, Ar—H); 6.93-6.95 (dd, 1H, Ar—H); 6.91-6.92 (m, 1H, Ar—H); 5.93 (s, 1H, OH); 4.86-4.89 (t, 1H, CHOH); 2.29-2.50 (m, 6H, CH$_2$N(CH$_2$CH$_2$)$_2$); 1.79-1.86 (m, 2H, HOCHCH$_2$CH$_2$N); 1.45-1.51 (m, 4H, N(CH$_2$ CH$_2$)$_2$CH$_2$); 1.38-1.42 (m, 2H, (CH$_2$CH$_2$)$_2$CH$_2$).

5.3: Preparation of 1-[3-(benzo[1,3]dioxolan-4-yl-oxy)-3-(thiophen-2-yl)-propyl]-piperidine.oxalate (compound I$_5$)

3-(Piperidin-1-yl)-1-(thiophen-2-yl)-1-propanol (2.25 g, 0.01 mol), 5-hydroxyl-benzo[1,4]dioxolane (1.38 g, 0.01 mol) and triphenylphosphine (3.93 g, 0.015 mol) were dissolved in 80 mL anhydrous tetrahydrofuran. The mixture was slowly added dropwise with the solution of diethyl azodicarboxylate (2.61 g, 0.015 mol) in 20 mL anhydrous tetrahydrofuran, and the reaction temperature was controlled by an ice-salt bath to be below −5° C. After completion of the addition, the ice-salt bath was removed. The reaction was performed at room temperature for 24 h. After the end of reaction, tetrahydrofuran was distilled out under a reduced pressure, and the obtained oily liquid was dissolved in 100 mL ethyl acetate. The mixture was washed with diluted sodium hydroxide aqueous solution and saturated sodium chloride aqueous solution respectively, dried over anhydrous sodium sulfate, and separated by silica gel column chromatography to obtain 1.45 g of a pale yellow oily liquid. The oily liquid was dissolved in 30 mL of ethyl acetate, added with oxalic acid (0.38 g, 0.042 mol) to generate a white solid. The mixture was heated to reflux, cooled to room temperature, frozen for 2 h, and filtrated under vacuum. The filter cake was washed with cooled ethyl acetate to obtain 1.53 g of the target compound as a white powdery solid in a yield of 35.2% and a melting point of 118-120° C. MS (m/e): 346.4 (M+H$^+$). $^1$H-NMR δ (ppm, DMSO-d$_6$): 7.47-7.48 (d, 1H, 5'-H); 7.10-7.11 (d, 1H, 3'-H); 6.95-6.97 (dd, 1H, 4'-H); 6.67-6.71 (t, 1H, 6-H); 6.58-6.60 (d, 1H, 7-H); 6.53-6.55 (d, 1H, 5-H); 5.97-5.98 (d, 2H, 2-H); 5.71-5.74 (t, 1H, CHO); 2.30-2.32 (m, 6H, CH$_2$N(CH$_2$CH$_2$)$_2$); 2.13-2.05 (m, 1H, HOCHCH$_2$CH$_2$N); 1.93-2.01 (m, 1H, HOCHCH$_2$CH$_2$N); 1.45-1.49 (m, 4H, N(CH$_2$CH$_2$)$_2$CH$_2$)); 1.35-1.37 (m, 2H, (CH$_2$CH$_2$)$_2$CH$_2$).

Example 6

Preparation of N,N-dimethyl-[3-(benzo[1,3]dioxolan-4-yl-oxy)-3-(furan-2-yl)]-propylamine.oxalate (compound I$_6$)

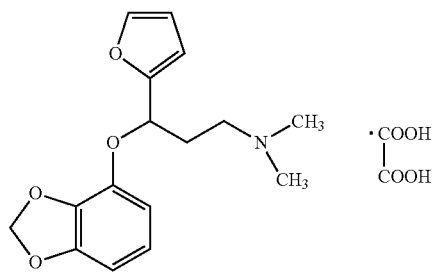

I$_6$ 6.1: Preparation of 3-dimethylamino-1-(furan-2-yl)-1-acetone.hydrochloride 2-acetylfuran (17.6 g, 0.16 mol), dimethylamine hydrochloride (16.8 g, 0.21 mol), paraformaldehyde (9.5 g, 0.32 mol) and 50 mL anhydrous ethanol were placed in a 150 mL three-necked bottle. The mixture was added dropwise with concentrated hydrochloric acid to reach a pH of 3-4 and heated to reflux for 8 h. The reaction was terminated, cooled to room temperature, frozen overnight, and filtrated under vacuum. The filter cake was washed with cold anhydrous ethanol to obtain 28.1 g of 3-dimethylamino-1-(furan-2-yl)-1-acetone hydrochloride as a pale yellow crystal in a yield of 86.4%. MS (m/e): 168.3 (M+1$^+$).

6.2: Preparation of 3-dimethylamino-1-(furan-2-yl)-1-propanol

3-Dimethylamino-1-(furan-2-yl)-1-acetone.hydrochloride (24.4 g, 0.12 mol) was dissolved in 120 mL distilled water. The mixture was added dropwise with 2.5M sodium hydroxide aqueous solution to reach a pH of 10, and extracted with ethyl acetate (80 mL×3). The organic phases were combined, washed with saturated sodium chloride aqueous solution twice, dried over anhydrous sodium sulfate, and distilled under a reduced pressure to remove ethyl acetate. The obtained yellow oily liquid was dissolved in 30 mL anhydrous tetrahydrofuran, added dropwise slowly into LiAlH$_4$ (6.7 g, 0.18 mol) in 100 mL anhydrous tetrahydrofuran solution, and the reaction temperature was controlled in an ice bath. After the addition, the ice bath was removed. The reaction was performed at room temperature for 2 h and then stopped. Into the reaction liquid, anhydrous ethanol was slowly added dropwise. After complete reaction of the residual LiAlH$_4$, solids were removed by filtration under vacuum, tetrahydrofuran was distilled out under a reduced pressure, and the residue was extracted with dichloromethane (50 mL×3). The organic phases were combined, washed with saturated sodium chloride aqueous solution twice, dried over anhydrous sodium sulfate, and distilled to remove dichloromethane to obtain 16.8 g of 3-dimethylamino-1-(furan-2-yl)-1-propanol as a yellow oily liquid in a yield of 82.6%. $^1$H-NMR δ (ppm, DMSO-d$_6$): 7.55 (s, 1H, Ar—H); 6.36-6.37 (m, 1H, Ar—H); 6.22-6.23 (d, 1H, Ar—H); 5.45 (s, 1H, OH); 4.56-4.59 (t, 1H, CHOH); 2.24-2.50 (m, 2H, CH$_2$N); 2.11 (s, 6H, N(CH$_3$)$_2$); 1.76-1.83 (m, 2H, CH$_2$CH$_2$N).

6.3: Preparation of N,N-dimethyl-[3-(benzo[1,3]dioxolan-4-yl-oxy)-3-(furan-2-yl)]propylamine.oxalate (compound I$_6$)

3-Dimethylamino-1-(furan-2-yl)-1-propanol (1.69 g, 0.01 mol), 4-hydroxyl-benzo[1,3]dioxolane (1.38 g, 0.01 mol) and triphenylphosphine (3.93 g, 0.015 mol) were dissolved in 80 mL anhydrous tetrahydrofuran. The mixture was slowly added dropwise with the solution of diethyl azodicarboxylate (2.61 g, 0.015 mol) in 20 mL anhydrous tetrahydrofuran, and the reaction temperature was controlled by an ice-salt bath to be below −5° C. After completion of the addition, the ice-bath was removed. The reaction was performed at room temperature for 24 h. After the end of reaction, tetrahydrofuran was distilled out under a reduced pressure, and the obtained oily liquid was dissolved in 100 mL ethyl acetate. The mixture was washed with diluted sodium hydroxide aqueous solution and saturated sodium chloride aqueous solution respectively, dried over anhydrous sodium sulfate, and separated by silica gel column chromatography to obtain 0.75 g of N,N-dimethyl-[3-(benzo[1,3]dioxolan-4-yl-oxy)-3-(furan-2-yl)]-propylamine as a pale yellow oily liquid. The oily liquid was dissolved in 20 mL ethyl acetate, and the mixture was added with 0.23 g (0.026 mol) of oxalic acid to generate a pale yellow solid, heated to reflux, cooled to room temperature, frozen for 2 h, and filtrated under vacuum. The filter cake was washed with cold ethyl acetate to obtain 0.88 g of the target compound as a pale yellow powdery solid in a yield of 23.2% and a melting point of 97-101° C. MS (m/e): 290.4 (M+1$^+$), 312.5 (M+Na$^+$). $^1$H-NMR δ (ppm, DMSO-d$_6$): 7.63-7.64 (dd, 1H, 5'-H); 6.62-6.66 (t, 1H, 6-H); 6.60-6.62 (d, 1H, 5-H); 6.55-6.57 (d, 1H, 7-H); 6.46-6.47 (d, 1H, 3'-H); 6.39-6.41 (dd, 1H, 4'-H); 5.95-5.97 (dd, 1H, 2-H); 5.44-5.47 (t, 1H, CHO); 2.24-2.28 (t, 2H, CH$_2$N); 1.99-2.19 (m, 2H, CH$_2$CH$_2$N); 2.11 (s, 6H, N(CH$_3$)$_2$).

Example 7

Preparation of N-methyl-[3-(benzo[1,3]dioxolan-4-yl-oxy)-3-(furan-2-yl)]propylamine.oxalate (compound I$_7$)

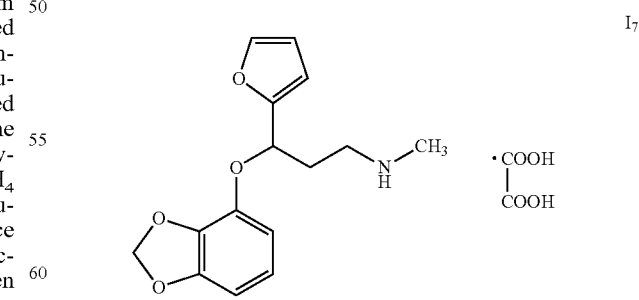

I$_7$

N,N-dimethyl-3-(benzo[1,3]dioxolan-4-yl-oxy)-3-(furan-2-ylpropylamine (0.59 g, 2.03 mmol) was dissolved in 30 mL anhydrous toluene. The mixture was heated to reflux, and added dropwise with phenyl chloroformate (0.38 g, 2.44 mmol) in 10 mL anhydrous toluene solution within 0.5 h.

After completion of the addition, the reflux was maintained for 1 h, and the reaction was then terminated, and cooled to room temperature. The organic phase was washed with 2.5M sodium hydroxide aqueous solution (20 mL×3), with distilled water to neutral, with 1.0M hydrochloric acid aqueous solution (20 mL×3), with distilled water to neutral, with saturated sodium chloride aqueous solution, and then dried over anhydrous sodium sulfate. The drying agent was removed by filtration, and toluene was removed by distillation under a reduced pressure to obtain a yellow oil.

30 mL 1,2-propylene glycol was added to the above yellow oil, and 0.81 g (2.03 mmol) sodium hydroxide dissolved in 8 mL distilled water was added to the above 1,2-propylene glycol solution. The mixture was heated to reflux for 3 h, cooled to room temperature after the end of reaction, added with diluted hydrochloric acid aqueous solution to reach a pH of about 3, stirred at room temperature to carry out the reaction for 1 h, extracted with n-hexane (20 mL×3), then added with sodium hydroxide aqueous solution to reach a pH of about 10, and extracted with ethyl actate (20 mL×3). The organic phase was washed with saturated saline aqueous solution, and dried over anhydrous sodium sulfate. The drying agent was removed by filtration, and the solvent was removed by distillation under vacuum to obtain a residue of about 15 mL. The residue was then added with 0.18 g (2.03 mmol) oxalic acid to generate a white precipitate. The mixture was heated to reflux for 0.5 h, cooled to room temperature, and frozen for 4 h. After filtration, the filter cake was washed with cold ethyl acetate to obtain 0.13 g of the target compound as a white powdery solid in a yield of 17.8% and a melting point of 130-133° C. MS (m/e): 276.1 (M+1$^+$), 298.0 (M+Na$^+$). $^1$H-NMR δ (ppm, DMSO-d$_6$): 7.63-7.64 (dd, 1H, 5'-H); 6.69-6.73 (t, 1H, 6-H); 6.62-6.64 (d, 1H, 5-H); 6.55-6.57 (d, 1H, 7-H); 6.46-6.47 (d, 1H, 3'-H); 6.40-6.41 (dd, 1H, 4'-H); 5.95-5.97 (dd, 1H, 2-H); 5.49-5.52 (t, 1H, CHO); 2.50-2.53 (t, 2H, CH$_2$N); 2.25 (s, 6H, NCH$_3$); 2.10-2.16 (m, H, CH$_2$CH$_2$N); 1.99-2.05 (m, H, CH$_2$CH$_2$N).

Example 8

Preparation of N,N-dimethyl-3-[(benzo[1,4]dioxan-5-yl-oxy)-3-(thiophen-2-yl)-propylamine].oxalate (compound I$_8$)

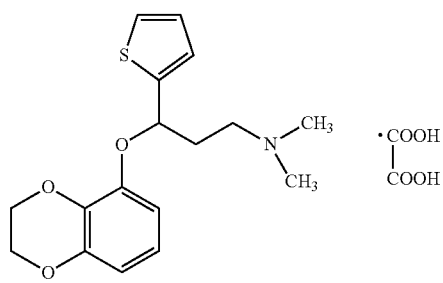

3-Dimethylamino-1-(thiophen-2-yl)-1-propanol (1.85 g, 0.01 mol), 5-hydroxyl-benzo[1,4]dioxane (1.52 g, 0.01 mol) and triphenylphosphine (3.93 g, 0.015 mol) were dissolved in 80 mL anhydrous tetrahydrofuran. The mixture was slowly added dropwise with the solution of diethyl azodicarboxylate (2.61 g, 0.015 mol) in 20 mL anhydrous tetrahydrofuran, and the reaction temperature was controlled by an ice-salt bath to be below −5° C. After completion of the addition, the ice-salt bath was removed, and the reaction was performed at room temperature for 24 h. After the reaction, tetrahydrofuran was distilled out under a reduced pressure, and the obtained oil liquid was dissolved in 100 mL ethyl acetate. The mixture was washed with diluted sodium hydroxide aqueous solution and saturated sodium chloride aqueous solution respectively, dried over anhydrous sodium sulfate, and separated by silica gel column chromatography to obtain 1.56 g of N,N-dimethyl-3-[(benzo[1,4]dioxan-5-yl-oxy)-3-(thiophen-2-yl)-propylamine] as a yellow oil. The yellow oil was dissolved in 50 mL ethyl acetate, the mixture was added with 0.41 g (0.045 mol) oxalic acid to generate a pale yellow precipitate, heated to reflux, cooled to room temperature, frozen for 2 h, and filtrated under vacuum. The filter cake was washed with cold ethyl acetate to obtain 1.69 g of the target compound as a pale yellow powdery solid in a yield of 39.1% and a melting point of 89-92° C. MS (m/e): 320.5 (M+1$^+$). $^1$H-NMR δ (ppm, CDCl$_3$-d$_3$): 7.22-7.24 (dd, 1H, 5'-H); 6.99-7.00 (d, 1H, 3'-H); 6.92-6.94 (dd, 1H, 4'-H); 6.61-6.65 (t, 1H, 7-H); 6.49-6.51 (d, 2H, 6,8-H); 5.48-5.51 (t, 1H, CHO); 4.23-4.31 (t, 4H, 2,3-H); 2.44-2.47 (t, 2H, CH$_2$N); 2.35-2.42 (m, 1H, CH$_2$CH$_2$N); 2.25 (s, 6H, N(CH$_3$)$_2$); 2.08-2.13 (m, 1H, CH$_2$CH$_2$N).

Example 9

Preparation of N-methyl-3-[(benzo[1,4]dioxan-5-yl-oxy)-3-(thiophen-2-yl)-propylamine]oxalate (compound I$_9$)

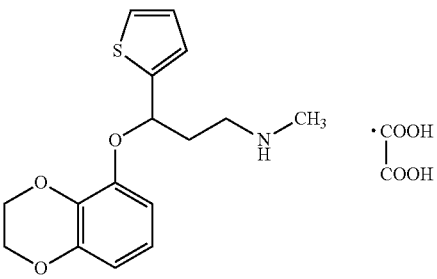

N,N-dimethyl-3-[(benzo[1,4]dioxan-5-yl-oxy)-3-(thiophen-2-yl)-propylamine] (0.78 g, 2.44 mmol) was dissolved in 50 mL anhydrous toluene. The mixture was heated to reflux, and added dropwise with the solution of phenyl chloroformate (0.46 g, 2.93 mmol) in 10 mL anhydrous toluene over 0.5 h. The reflux was maintained for 1 h after completion of the addition, and then the reaction was terminated, and cooled to room temperature. The organic phase was washed with 2.5M sodium hydroxide aqueous solution (20 mL×3), with distilled water to neutral, then with 1.0M hydrochloric acid aqueous solution (20 mL×3), with distilled water to neutral, with saturated sodium chloride aqueous solution, and dried over anhydrous sodium sulfate. The drying agent was removed by filtration, and toluene was distilled out under a reduced pressure to obtain a yellow oil.

30 mL of 1,2-propylene glycol was added to the above yellow oil, and sodium hydroxide (0.98 g, 2.44 mmol) dissolved in 8 mL of distilled water was to added into the above 1,2-propylene solution. The mixture was heated to reflux for 3 h, the reaction was terminated, cooled to room temperature, added with diluted hydrochloric acid aqueous solution to reach a pH of about 3, stirred to perform the reaction at room temperature for 1 h, extracted with n-hexane (20 mL×3), then added with sodium hydroxide aqueous solution to reach a pH of about 10, and extracted with ethyl acetate (20 mL×3). The organic phase was washed with saturated saline aqueous solution, dried over anhydrous sodium sulfate, filterated to remove the drying agent, distilled under vacuum to remove solvent and obtain a residue of about 15 mL. The residue was added with 0.22 g (2.44 mmol) of oxalic acid to generate a white precipitate. The mixture was heated to reflux for 0.5 h, cooled to room temperature, and frozen for 4 h. After filtration under vacuum, the filter cake was washed with cold ethyl acetate to obtain 0.30 g of the target compound as a pale yellow powdery solid in a yield of 31.4% and a melting point of 128-131° C. MS (m/e): 306.4 (M+H$^+$), 328.1 (M+Na$^+$) $^1$H-NMR δ (ppm, DMSO-d$_6$): 7.45-7.46 (dd, 1H, 5'-H); 7.09-7.10 (dd, 1H, 3'-H); 6.95-6.97 (dd, 1H, 4'-H); 6.58-6.62 (t, 1H, 7-H); 6.51-6.53 (d, 1H, 8-H); 6.41-6.43 (d, 1H, 6-H); 5.63-5.66 (t, 1H, CHO); 4.20-4.24 (m, 4H, 2,3-H); 2.52-2.56 (t, 2H, CH$_2$N); 2.26 (s, 3H, NCH$_3$); 2.12-2.16 (m, 1H, C$\underline{H}_2$CH$_2$N); 1.95-1.99 (m, 1H, C$\underline{H}_2$CH$_2$N).

Example 10

Preparation of N,N-dimethyl-3-[(benzo[1,4]dioxan-5-yl-oxy)-3-(furan-2-yl)propylamine].oxalate (compound $I_{10}$)

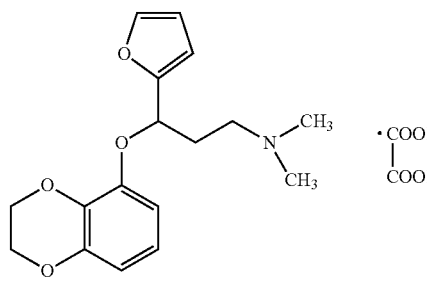

$I_{10}$

3-Dimethylamino-1-(furan-2-yl)-1-propanol (1.69 g, 0.01 mol), 5-benzo[1,4]dioxane (1.52 g, 0.01 mol) and triphenylphosphine (3.93 g, 0.015 mol) was dissolved in 80 mL anhydrous tetrahydrofuran. The mixture was slowly added dropwise with the solution of diethyl azodicarboxylate (2.61 g, 0.015 mol) in 20 mL anhydrous tetrahydrofuran, and the reaction temperature was controlled by an ice-salt bath to be below −5° C. After completion of the addition, the ice-salt bath was removed, and the reaction was performed at room temperature for 24 h. After the reaction, tetrahydrofuran was distilled out under a reduced pressure, and the obtained oily liquid was dissolved in 100 mL ethyl acetate. The mixture was washed with diluted sodium hydroxide aqueous solution and saturated sodium chloride aqueous solution respectively, dried over anhydrous sodium sulfate, and separated by silica gel column chromatography to obtain 0.98 g of N,N-dimethyl-3-[(benzo[1,4]dioxan-5-yl-oxy)-3-(furan-2-yl)propylamine] as a yellow oil. The yellow oil was dissolved in 30 mL ethyl acetate, and added with oxalic acid (0.29 g, 0.032 mol) to generate a pale yellow precipitate. The mixture was heated to reflux, cooled to room temperature, frozen for 2 h, and filtrated under vacuum. The filter cake was washed with cold ethyl acetate to obtain 0.75 g of the target compound as a pale yellow powdery solid in a yield of 19.1% and a melting point of 101-103° C. MS (m/e): 304.3 (M+1$^+$), 326.2 (M+Na$^+$). $^1$H-NMR δ (ppm, DMSO-d$_6$): 7.63 (s, 1H, 5'-H); 6.62-6.66 (t, 1H, 7-H); 6.54-6.56 (d, 1H, 6-H); 6.44-6.46 (d, 1H, 8-H); 6.39-6.40 (m, 2H, 3',4'-H); 5.30-5.34 (t, 1H, CHO); 4.16-4.23 (t, 4H, 2,3-H); 2.23-2.27 (t, 2H, CH$_2$N); 1.99-2.23 (m, 2H, C$\underline{H}_2$CH$_2$N); 2.10 (s, 6H, N(CH$_3$)$_2$).

Example 11

Antidepressant Effect of the Target Compounds as Measured by Tail Suspension Test in Mice Male ICR mice (SPF grade) weighing 18-22 g each was suspended by clampping separately at 1 cm from the end of the tail with a clamp attached to a rope at the center of top plate of a 25×25×25 cm tail suspension box, and the head is away from the box bottom by 4-5 cm. The mice were administrated via intraperitoneal injection at 30 min before the test or via intragastric administration at 60 min before the test with the compound to be tested and Duloxetine as the positive control. The tail was suspended for 6 min, and the immobility time of mice during the last 4 min was accumulated. The results of antidepressant effects of the target compounds administrated via intraperitoneal injection as determined by the tail suspension test in mice are given in Table 1.

TABLE 1

Effects of the target compounds administrated via intraperitoneal injection on the immobility time of the tail suspended mice

| Dose (mg/kg, i.p.) | immobility time (s) | | | | |
|---|---|---|---|---|---|
| | Duloxetine | $I_1$ | $I_2$ | $I_6$ | $I_7$ |
| 0 | | 80.6-108.7 | | | |
| 2.5 | Not tested | 38.2 ± 32.5* | 35.0 ± 30.0$^\#$ | 51.2 ± 34.3$^\#$ | 30.7 ± 44.1$^\#$ |
| 5 | Not tested | 20.2 ± 17.1$^\#$ | 20.8 ± 32.1$^\#$ | 53.9 ± 46.9$^\#$ | 21.9 ± 21.5$^\#$ |
| 10 | 35.9-49.2 | 6.2 ± 7.4$^\#$ | 1.9 ± 4.0$^\#$ | 22.5 ± 28.1$^\#$ | 33.3 ± 31.2$^\#$ |
| 20 | Not tested | 2.0 ± 6.3$^\#$ | 2.5 ± 4.1$^\#$ | 11.9 ± 16.8$^\#$ | 0.3 ± 0.95$^\#$ |

As compared to the solvent control group:
*p < 0.05,
$^\#$p < 0.01

In the tail-suspended model of mice, the antidepressant effect was evaluated by observing the immobility time of the tail-suspended mice, and the shorter the immobility time, the stronger the antidepressant effect. As seen from Table 1, the target compounds can significantly shorten the immobility time; under the same dose, the target compounds have more significant antidepressant effect than Duloxetine; and with increasing of the dose, more significant effect on the immobility time was observed, indicating that their antidepressant effects are explicitly dose dependent.

The antidepressant effect of compound $I_2$ was evaluated via intragastric administration and the results thereof are shown in Table 2.

TABLE 2

Effect of the target compound via intragastric administration on the immobility time of tail-suspended mice

| Dose | Immobility time (s) | |
| --- | --- | --- |
| (mg/kg, i.g.) | Duloxetine | $I_2$ |
| 0 | 135.4 ± 28.3 | 135.4 ± 28.3 |
| 5 | Not tested | 66.1 ± 44.9# |
| 10 | 81.0 ± 44.7* | 51.8 ± 36.0# |
| 20 | Not tested | 22.0 ± 16.9# |

As compared to the solvent control group:
*p < 0.05,
p < 0.0

Table 2 shows that compound $I_2$ can significantly shorten the immobility time of the tail-suspended mice via intragastric administration; its at the dose of 5 mg/kg is remarkably greater than that of duloxetine at the dose of 10 mg/kg; and the higher the dose, the greater the effect on the immobility time, which indicates that its antidepressant effect is explicitly dose dependent.

Example 12

The Antidepressant Effect of the Target Compounds as Measured by Forced Swim Test in Mice Mail ICR mice (SPF grade) weighing 18-22 g were placed in a glass jar (diameter 10 cm, and height 20 cm) with water 10 cm in depth and a temperature of 25° C., observed for 6 min, and the accumulated immobility time of mice (i.e., the time that the animal has no motion or a slight motion in its hind limbs, but maintains body floated without motion) during the last 4 min was recorded. The mice were administrated with the compound to be tested and Duloxetine as the positive control drug via intraperitoneal injection at 30 min before the test or via intragastric administration at 60 min before the test. The effects of the target compounds on the immobility time of the forced swim mice via intraperitoneal injection are given in Table 3.

In the forced swim model of mice, the antidepressant effect was evaluated to by observing the immobility time of the forced swim mice, and the shorter the immobility time, the stronger the antidepressant effect. As seen from Table 3, the target compounds can significantly shorten the immobility time; at the same dose, the antidepressant effects of the target compounds are significantly greater than that of the Duloxetine; and the higher the dose, the greater the effect on the immobility time, which indicates that their antidepressant effects are explicitly dose dependent.

The antidepressant effect of compound $I_2$ was further evaluated via intragastric administration, and the results thereof are shown in Table 4.

TABLE 4

Effect of the target compound on the immobility time of the forced swim mice via intragastric administration

| Dose | Immobility time (s) | |
| --- | --- | --- |
| (mg/kg, i.g.) | Duloxetine | $I_2$ |
| 0 | 144.6 ± 53.4 | 144.6 ± 53.4 |
| 5 | Not tested | 104.1 ± 39.7 |
| 10 | Not tested | 83.7 ± 34.2* |
| 20 | Not tested | 60.1 ± 33.8# |
| 40 | 60.5 ± 44.1# | Not tested |

As compared to the solvent control group:
*p < 0.05,
p < 0.01

Table 4 shows that compound $I_2$ can significantly shorten the immobility time via intragastric administration; its antidepressant effect at the dose of 20 mg/kg is comparable to that of Duloxetine at the dose of 40 mg/kg; and the higher the dose, the greater the effect on the immobility time, which indicates that its antidepressant effect is explicitly dose dependent.

TABLE 3

Effects of the target compounds on the immobility time of the forced swim mice via intraperitoneal injection

| Dose | Immobility time (s) | | | | |
| --- | --- | --- | --- | --- | --- |
| (mg/kg, i.p.) | Duloxetine | $I_1$ | $I_2$ | $I_6$ | $I_7$ |
| 0 | | | 115.4-150.2 | | |
| 2.5 | Not tested | 148.7 ± 40.3 | 113.6 ± 47.4 | 92.4 ± 39.2 | 94.3 ± 55.3 |
| 5 | Not tested | 86.7 ± 44.7# | 119.4 ± 47.0 | 96.5 ± 43.3 | 78.9 ± 43.1 |
| 10 | Not tested | 54.6 ± 44.0# | 86.1 ± 36.5* | 108.2 ± 46.7 | 70.9 ± 33.0* |
| 20 | 96.7-135.4 | 18.6 ± 15.7# | 43.1 ± 37.1# | 61.2 ± 44.5* | 28.4 ± 35.8# |

As compared to the solvent control group:
*p < 0.05,
p < 0.01

What is claimed is:

1. An amine compound represented by Formula I:

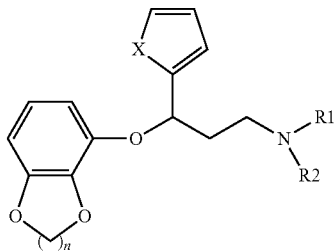

wherein,
X represents S or O;
$R_1$ and $R_2$ independently represent H or $C_{1-4}$-alkyl, or $R_1$ and $R_2$ together with the nitrogen atom to which they are attached form a 5- or 6-membered heterocyclic ring; and
n is 1 or 2,
or a pharmaceutically acceptable salt thereof.

2. The compound of claim 1, wherein,
X represents S or O;
$R_1$ and $R_2$ independently represent H or $C_{1-4}$-alkyl; and
n is 1 or 2.

3. The compound of claim 1, wherein,
X represents S or O;
$R_1$ and $R_2$ independently represent H, methyl or ethyl; and
n is 1 or 2.

4. The compound of claim 1, wherein,
X represents S or O;
$R_1$ and $R_2$ together with the nitrogen atom to which they are attached form pyrrole ring or piperidine ring; and
n is 1 or 2.

5. The compound of claim 1, wherein the pharmaceutically acceptable salt is oxalate.

6. The compound of claim 1, which is selected from the group consisting of:
N,N-dimethyl-3-[(benzo[1,3]dioxolan-4-yl)-oxy]-3-(thiophen-2-yl)-propylamine.oxalate;
N-methyl-3-[(benzo[1,3]dioxolan-4-yl)-oxy]-3-(thiophen-2-yl)-propylamine oxalate;
N,N-diethyl-3-[(benzo[1,3]dioxolan-4-yl)-oxy]-3-(thiophen-2-yl)-propylamine.oxalate;
1-[3-(benzo[1,3]dioxolan-4-yl-oxy)-3-(thiophen-2-yl)-propyl]-pyrrolidine.oxalate;
1-[3-(benzo[1,3]dioxolan-4-yl-oxy)-3-(thiophen-2-yl)-propyl]-piperidine.oxalate;
N,N-dimethyl-[3-(benzo[1,3]dioxolan-4-yl-oxy)-3-(furan-2-yl)]propylamine.oxalate;
N-methyl-[3-(benzo[1,3]dioxolan-4-yl-oxy)-3-(furan-2-yl)]-propylamine.oxalate;
N,N-dimethyl-3-[(benzo[1,4]dioxan-5-yl-oxy)-3-(thiophen-2-yl)-propylamine].oxalate;
N-methyl-3-[(benzo[1,4]dioxan-5-yl-oxy)-3-(thiophen-2-yl)-propylamine].oxalate; and
N,N-dimethyl-3-[(benzo[1,4]dioxan-5-yl-oxy)-3-(furan-2-yl)propylamine].oxalate.

7. A pharmaceutical composition comprising the compound of any one of claims 1 to 6 together with one or more pharmaceutically acceptable carriers or excipients.

8. A method for treating depression in a subject by administering to the subject the compound of any one of claims 1 to 6 together with one or more pharmaceutically acceptable carriers or excipients.

* * * * *

UNITED STATES PATENT AND TRADEMARK OFFICE
CERTIFICATE OF CORRECTION

PATENT NO.         : 8,318,772 B2
APPLICATION NO.    : 13/001379
DATED              : November 27, 2012
INVENTOR(S)        : Bohua Zhong et al.

It is certified that error appears in the above-identified patent and that said Letters Patent is hereby corrected as shown below:

In the Claims:

Column 21, Lines 2-16:
"1. An amine compound represented by Formula I:

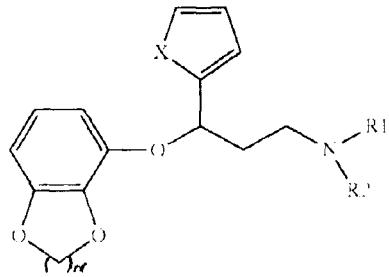

wherein," should read,

--1. An Amine compound represented by Formula I:

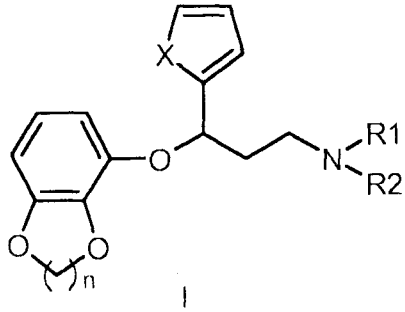

wherein,--.

Column 21, Line 18:
"$R_1$ and $R_2$ independently represent H or $C_{1-4}$-alkyl, or $R_1$" should read, --$R_1$ and $R_2$ independently represent H or $C_{1-4}$alkyl, or $R_1$--.

Signed and Sealed this
Fifteenth Day of April, 2014

Michelle K. Lee
*Deputy Director of the United States Patent and Trademark Office*

CERTIFICATE OF CORRECTION (continued)

Column 21, Line 25:
"$R_1$ and $R_2$ independently represent H or $C_{1-4}$-alkyl; and" should read, --$R_1$ and $R_2$ independently represent H or $C_{1-4}$alkyl; and--.

Column 22, Lines 5-24:
"N,N-dimethyl-3-[(benzo[1,3]dioxolan-4-yl)-oxy]-3-(thiophen-2-yl)-propylamine.oxalate; N-methyl-3-[(benzo[1,3]dioxolan-4-yl)-oxy]-3-(thiophen-2-yl)-propylamine.oxalate; N,N-diethyl-3-[(benzo[1,3]dioxolan-4-yl)-oxy]-3-(thiophen-2-yl)-propylamine.oxalate: 1-[3-(benzo[1,3]dioxolan-4-yl-oxy)-3-(thiophen-2-yl)-propyl]-pyrrolidine.oxalate; 1-[3-(benzo[1,3]dioxolan-4-yl-oxy)-3-(thiophen-2-yl)-propyl]-piperidine.oxalate; N,N-dimethyl-[3-(benzo[1,3]dioxolan-4-yl-oxy)-3-(furan-2-yl)] propylamine.oxalate; N-methyl-[3-(benzo[1,3]dioxolan-4-yl-oxy)-3-(furan-2-yl)]-propylamine.oxalate; N,N-dimethyl-3-[(benzo[1,4]dioxan-5-yl-oxy)-3-(thiophen-2-yl)-propylamine].oxalate; N-methyl-3-[(benzo[1,4]dioxan-5-yl-oxy)-3-(thiophen-2-yl)-propylamine].oxalate; and N,N-dimethyl-3-[(benzo[1,4]dioxan-5-yl-oxy)-3-(furan-2-yl)propylamine].oxalate." should read,
--N,N-dimethyl-3-[(benzo[1,3]dioxolan-4-yl)-oxy]-3-(thiophen-2-yl)-propylamine·oxalate; N-methyl-3-[(benzo[1,3]dioxolan-4-yl)-oxy]-3-(thiophen-2-yl)-propylamine·oxalate; N,N-diethyl-3-[(benzo[1,3]dioxolan-4-yl)-oxy]-3-(thiophen-2-yl)-propylamineoxalate; 1-[3-(benzo[1,3]dioxolan-4-yl-oxy)-3-(thiophen-2-yl)-propyl]-pyrrolidine·oxalate; 1-[3-(benzo[1,3]dioxolan-4-yl-oxy)-3-(thiophen-2-yl)-propyl]-piperidine·oxalate; N,N-dimethyl-[3-(benzo[1,3]dioxolan-4-yl-oxy)-3-(furan-2-yl)] propylamine·oxalate; N-methyl-[3-(benzo[1,3]dioxolan-4-yl-oxy)-3-(furan-2-yl)]-propylamine·oxalate; N,N-dimethyl-3-[(benzo[1,4]dioxan-5-yl-oxy)-3-(thiophen-2-yl)-propylamine]·oxalate; N-methyl-3-[(benzo[1,4]dioxan-5-yl-oxy)-3-(thiophen-2-yl)-propylamine]·oxalate; and N,N-dimethyl-3-[(benzo[1,4]dioxan-5-yl-oxy)-3-(furan-2-yl)propylamine]·oxalate.--.